United States Patent
Vogel

(10) Patent No.: US 10,449,069 B2
(45) Date of Patent: Oct. 22, 2019

(54) STENT

(71) Applicant: Covidien LP, Mansfield, MA (US)

(72) Inventor: Jeffrey Vogel, Brooklyn Park, MN (US)

(73) Assignee: Covidien LP, Mansfield, MA (US)

( * ) Notice: Subject to any disclaimer, the term of this patent is extended or adjusted under 35 U.S.C. 154(b) by 43 days.

(21) Appl. No.: 15/351,082

(22) Filed: Nov. 14, 2016

(65) Prior Publication Data

US 2018/0133039 A1    May 17, 2018

(51) Int. Cl.
*A61F 2/915* (2013.01)
*A61F 2/844* (2013.01)

(52) U.S. Cl.
CPC .............. *A61F 2/915* (2013.01); *A61F 2/844* (2013.01); *A61F 2002/91525* (2013.01); *A61F 2002/91541* (2013.01); *A61F 2002/91575* (2013.01)

(58) Field of Classification Search
USPC .................................................... 623/1.1–3.1
See application file for complete search history.

(56) References Cited

U.S. PATENT DOCUMENTS

| | | |
|---|---|---|
| 5,354,308 A | 10/1994 | Simon et al. |
| 5,707,386 A | 1/1998 | Schnepp-Pesch et al. |
| 5,718,713 A | 2/1998 | Frantzen |
| 5,759,192 A | 6/1998 | Saunders |
| 5,827,321 A | 10/1998 | Roubin et al. |
| 5,843,164 A | 12/1998 | Frantzen et al. |
| 5,843,175 A * | 12/1998 | Frantzen ............ A61F 2/91 623/1.15 |
| 5,860,999 A | 1/1999 | Schnepp-Pesch et al. |
| 5,902,317 A | 5/1999 | Kleshinski et al. |
| 6,042,606 A | 3/2000 | Frantzen |

(Continued)

FOREIGN PATENT DOCUMENTS

| | | |
|---|---|---|
| CN | 1479596 | 3/2004 |
| CN | 101385669 | 3/2009 |

(Continued)

OTHER PUBLICATIONS

PCT/US2017/061210, The International Search Report and the Written Opinion of the International Searching Authority, dated Feb. 16, 2018, 14pgs.

(Continued)

*Primary Examiner* — Yashita Sharma

(57) ABSTRACT

A stent includes a stent body defining a longitudinal axis and proximal and distal ends. The stent body is expandable from a compressed configuration to an expanded configuration and includes a plurality of stent segments including first and second end segments on opposite ends of the stent body and at least one intermediate segment disposed between the first end segment and the second end segment. Each stent segment defines a plurality of cells. The first end segment defines a plurality of peaks and valleys. The distance between a peak and an adjacent valley of the first end segment is substantially equal to a first length. The at least one intermediate segment defines a plurality of peaks and valleys. The distance between a peak and an adjacent valley of the at least one intermediate segment is substantially equal to a second length that is longer than the second length.

24 Claims, 5 Drawing Sheets

(56) References Cited

U.S. PATENT DOCUMENTS

| | | | |
|---|---|---|---|
| 6,106,548 A | 8/2000 | Roubin et al. | |
| 6,190,406 B1 | 2/2001 | Duerig et al. | |
| 6,306,141 B1 | 10/2001 | Jervis | |
| 6,312,459 B1 | 11/2001 | Huang et al. | |
| 6,348,065 B1 | 2/2002 | Brown et al. | |
| 6,358,274 B1 | 3/2002 | Thompson | |
| 6,558,415 B2 | 5/2003 | Thompson | |
| 6,623,518 B2 | 9/2003 | Thompson et al. | |
| 6,699,278 B2 | 3/2004 | Fischel et al. | |
| 6,755,856 B2 | 6/2004 | Fierens et al. | |
| 6,814,746 B2 | 11/2004 | Thompson et al. | |
| 6,818,014 B2 | 11/2004 | Brown et al. | |
| 6,863,685 B2 | 3/2005 | Davila et al. | |
| 6,913,619 B2 | 7/2005 | Brown et al. | |
| 6,962,603 B1 | 11/2005 | Brown et al. | |
| 6,981,986 B1* | 1/2006 | Brown | A61F 2/91 623/1.16 |
| 7,147,660 B2 | 12/2006 | Chobotov et al. | |
| 7,147,661 B2 | 12/2006 | Chobotov et al. | |
| 7,316,711 B2 | 1/2008 | Allen et al. | |
| 7,329,277 B2 | 2/2008 | Addonizio et al. | |
| 7,473,275 B2 | 1/2009 | Marquez | |
| 7,625,400 B2 | 12/2009 | Bowe et al. | |
| 7,655,033 B2 | 2/2010 | Fearnot et al. | |
| 7,753,948 B2 | 7/2010 | Roeder et al. | |
| 7,766,954 B2 | 8/2010 | Chobotov et al. | |
| 7,993,388 B2 | 8/2011 | Lee et al. | |
| 8,114,149 B2 | 2/2012 | Fischell et al. | |
| 8,167,927 B2 | 5/2012 | Chobotov | |
| 8,187,396 B2 | 5/2012 | Parker | |
| 8,211,162 B2 | 7/2012 | Tischler et al. | |
| 8,236,043 B2 | 8/2012 | Caro et al. | |
| 8,241,346 B2 | 8/2012 | Chobotov | |
| 8,328,864 B2 | 12/2012 | Niermann | |
| 8,328,865 B2 | 12/2012 | Bales, Jr. et al. | |
| 8,333,799 B2 | 12/2012 | Bales, Jr. et al. | |
| 8,382,816 B2 | 2/2013 | Pollock et al. | |
| 8,597,343 B2 | 12/2013 | Bliss et al. | |
| 8,628,565 B2 | 1/2014 | Ta et al. | |
| 8,658,081 B2 | 2/2014 | Gale et al. | |
| 9,180,031 B2 | 11/2015 | Vogel et al. | |
| 9,259,335 B2 | 2/2016 | Vogel et al. | |
| 9,610,180 B2 | 4/2017 | Cam et al. | |
| 2004/0138737 A1 | 7/2004 | Davidson et al. | |
| 2004/0167635 A1 | 8/2004 | Yachia et al. | |
| 2006/0015173 A1 | 1/2006 | Clifford et al. | |
| 2007/0050011 A1 | 3/2007 | Klein | |
| 2007/0061003 A1 | 3/2007 | Shmulewitz et al. | |
| 2007/0100434 A1 | 5/2007 | Gregorich et al. | |
| 2007/0239263 A1 | 10/2007 | Fliedner | |
| 2008/0221661 A1 | 9/2008 | Bidne et al. | |
| 2009/0105809 A1 | 4/2009 | Lee et al. | |
| 2009/0118810 A1 | 5/2009 | Klein et al. | |
| 2010/0137974 A1 | 6/2010 | Chouinard et al. | |
| 2012/0165920 A1 | 6/2012 | Meyer et al. | |
| 2012/0226346 A1* | 9/2012 | Boismier | A61F 2/915 623/1.16 |
| 2014/0067045 A1 | 3/2014 | Wack et al. | |
| 2014/0128959 A1 | 5/2014 | Gale et al. | |
| 2014/0277379 A1 | 9/2014 | Vogel et al. | |
| 2014/0277380 A1 | 9/2014 | Vogel et al. | |
| 2015/0105852 A1 | 4/2015 | Noffke et al. | |
| 2015/0297378 A1 | 10/2015 | Senness et al. | |
| 2016/0022453 A1 | 1/2016 | Vogel et al. | |
| 2016/0120670 A1 | 5/2016 | Vogel et al. | |

FOREIGN PATENT DOCUMENTS

| | | |
|---|---|---|
| CN | 101516291 | 8/2009 |
| DE | 10144430 A1 | 3/2003 |
| DE | 102007060497 A1 | 6/2009 |
| EP | 1523959 A2 | 4/2005 |
| WO | 9725937 A1 | 7/1997 |
| WO | 2004/028571 A2 | 4/2004 |
| WO | 2007005800 A1 | 1/2007 |
| WO | 2007013102 A1 | 2/2007 |
| WO | 2008005535 A2 | 1/2008 |
| WO | 2009/137993 A1 | 11/2009 |
| WO | 2012096716 A2 | 7/2012 |
| WO | 2012143731 A1 | 10/2012 |

OTHER PUBLICATIONS

PCT/US2017/061209, The International Search Report and the Written Opinion of the International Searching Authority, dated Feb. 16, 2018, 14 pgs.

U.S. Appl. No. 15/351,052, naming Jeffrey Vogel et al., filed Nov. 14, 2016.

U.S. Appl. No. 15/351,007, naming Jeffrey Vogel et al., filed Nov. 14, 2016.

* cited by examiner

STENT

TECHNICAL FIELD

This disclosure relates to a medical device and, in particular, to a stent.

BACKGROUND

Stents are widely used for numerous medical applications where the stent is placed in the lumen of a subject and expanded. Stents may be used in the coronary or the peripheral vasculature, as well as other body lumens. In some examples, stents are metal, tubular structures which are passed through a body lumen in a collapsed state. At the point of an obstruction or other deployment site in the body lumen, the stent is expanded to support the lumen. Stents may be self-expanding or balloon-expandable. Self-expanding stents may be inserted in a constrained state into a body lumen via a delivery device and released such that the unconstrained stent is free to radially expand. A balloon-expandable stent may be positioned on a balloon of a balloon catheter, and the stent may be expanded at the deployment site through inflation of the balloon.

SUMMARY

In some aspects, this disclosure describes example stents, which may be vascular stents or arterial stents. A stent may include a stent body defining a longitudinal axis and proximal and distal ends. The stent body may be expandable from a compressed configuration to an expanded configuration. The stent body may include a plurality of stent segments. The stent segments may include a first end segment and a second end segment on opposite ends of the stent body and at least one intermediate segment disposed between the first end segment and the second end segment. Each stent segment may define a plurality of cells. The first end segment may define a plurality of peaks and valleys. The distance between at a peak and an adjacent valley of the first end segment, which may be a proximal or distal end segment, may be substantially equal to a first length. The at least one intermediate segment may define a plurality of peaks and valleys. The distance between a peak and an adjacent valley of the at least one intermediate segment may be substantially equal to a second length. The first length may be longer than the second length.

In some examples, the example stents may be formed by a method including selecting an appropriate diameter tube, forming the stent pattern described above in a tubular member to form the stent body, incrementally expanding and heat setting the tubular member, and heat setting the tube at its final diameter.

Clause 1: In some examples, a stent comprises a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. The first end segment defines a plurality of peaks and valleys. The distance between a peak and an adjacent valley of the first end segment is substantially equal to a first length. The at least one intermediate segment defines a plurality of peaks and valleys. The distance between a peak and an adjacent valley of the at least one intermediate segment is substantially equal to a second length. The first length may be longer than the second length.

Clause 2: In some examples of the stent of clause 1, the first length is approximately two times the second length.

Clause 3: In some examples of the stent of clause 1 or 2, the first length is 1.5-3 times the second length.

Clause 4: In some examples of the stent of any of clauses 1-3, each stent segment defines the same number of cells.

Clause 5: In some examples of the stent of any of clauses 1-4, each stent segment defines the same number of peaks and valleys.

Clause 6: In some examples of the stent any of clauses 1-5, a portion of the first end segment defining only one cell defines only four peaks, only three valleys, and only two half valleys on each of two opposing sides of the portion of the first end segment.

Clause 7: In some examples of the stent of any of clauses 1-6, a portion of the at least one intermediate segment defining only one cell defines only four peaks, only three valleys, and only two half valleys on each of two opposing sides of the portion of the intermediate segment.

Clause 8: In some examples, a method comprises forming a stent pattern in a tubular member to form a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. The first end segment defines a plurality of peaks and valleys. The distance between a peak and an adjacent valley of the first end segment is substantially equal to a first length. The at least one intermediate segment defines a plurality of peaks and valleys. The distance between a peak and an adjacent valley of the at least one intermediate segment is substantially equal to a second length. The first length is longer than the second length.

Clause 9: In some examples of the method of clause 8, the tubular member comprises shape-memory material.

Clause 10: In some examples of the method of clause 8 or 9, the method further comprises incrementally expanding and heat setting the tubular member.

Clause 11: In some examples of the method of any of clauses 8-10, the first length is approximately two times the second length.

Clause 12: In some examples of the method of any of clauses 8-11, the first length is 1.5-3 times the second length.

Clause 13: In some examples of the method of any of clauses 8-12, each stent segment defines the same number of cells.

Clause 14: In some examples of the method of any of clauses 8-13, each stent segment defines the same number of peaks and valleys.

Clause 15: In some examples of the method of any of clauses 8-14, a portion of the first end segment defining only one cell defines only four peaks, only three valleys, and only two half valleys on each of two opposing sides of the portion of the first end segment.

Clause 16: In some examples of the method of any of clauses 8-15, a portion of the at least one intermediate segment defining only one cell defines only four peaks, only three valleys, and only two half valleys on each of two opposing sides of the portion of the intermediate segment.

Clause 17: In some examples, a method comprises advancing a distal end of a catheter to a treatment site within a patient, wherein a stent is disposed within the catheter; and releasing the stent from the catheter at the treatment site. The stent comprises a stent body defining a longitudinal axis and proximal and distal ends. The stent body is expandable from a compressed configuration to an expanded configuration. The stent body includes a plurality of stent segments. The stent segments include a first end segment and a second send segment on opposite ends of the stent body and at least one intermediate segment disposed between the first end segment and the second end segment. Each stent segment defines a plurality of cells. The first end segment defines a plurality of peaks and valleys. The distance between a peak and an adjacent valley of the first end segment is substantially equal to a first length. The at least one intermediate segment defines a plurality of peaks and valleys. The distance between a peak and an adjacent valley of the at least one intermediate segment is substantially equal to a second length. The first length is longer than the second length.

Clause 18: In some examples of the method of clause 17, the method further comprises inserting a guide member into a body lumen of the patient; and advancing the distal end of the catheter to the treatment site over the guide member.

Clause 19: In some examples of the method of clause 17 or 18, the first length is approximately two times the second length.

Clause 20: In some examples of the method of any of clauses 17-19, the first length is 1.5-3 times the second length.

Clause 21: In some examples of the method of any of clauses 17-20, each stent segment defines the same number of cells.

Clause 22: In some examples of the method of any of clauses 17-21, each stent segment defines the same number of peaks and valleys.

Clause 23: In some examples of the method of any of clauses 17-22, a portion of the first end segment defining only one cell defines only four peaks, only three valleys, and only two half valleys on each of two opposing sides of the portion of the first end segment.

Clause 24: In some examples of the method of any of clauses 17-23, a portion of the at least one intermediate segment defining only one cell defines only four peaks, only three valleys, and only two half valleys on each of two opposing sides of the portion of the intermediate segment.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
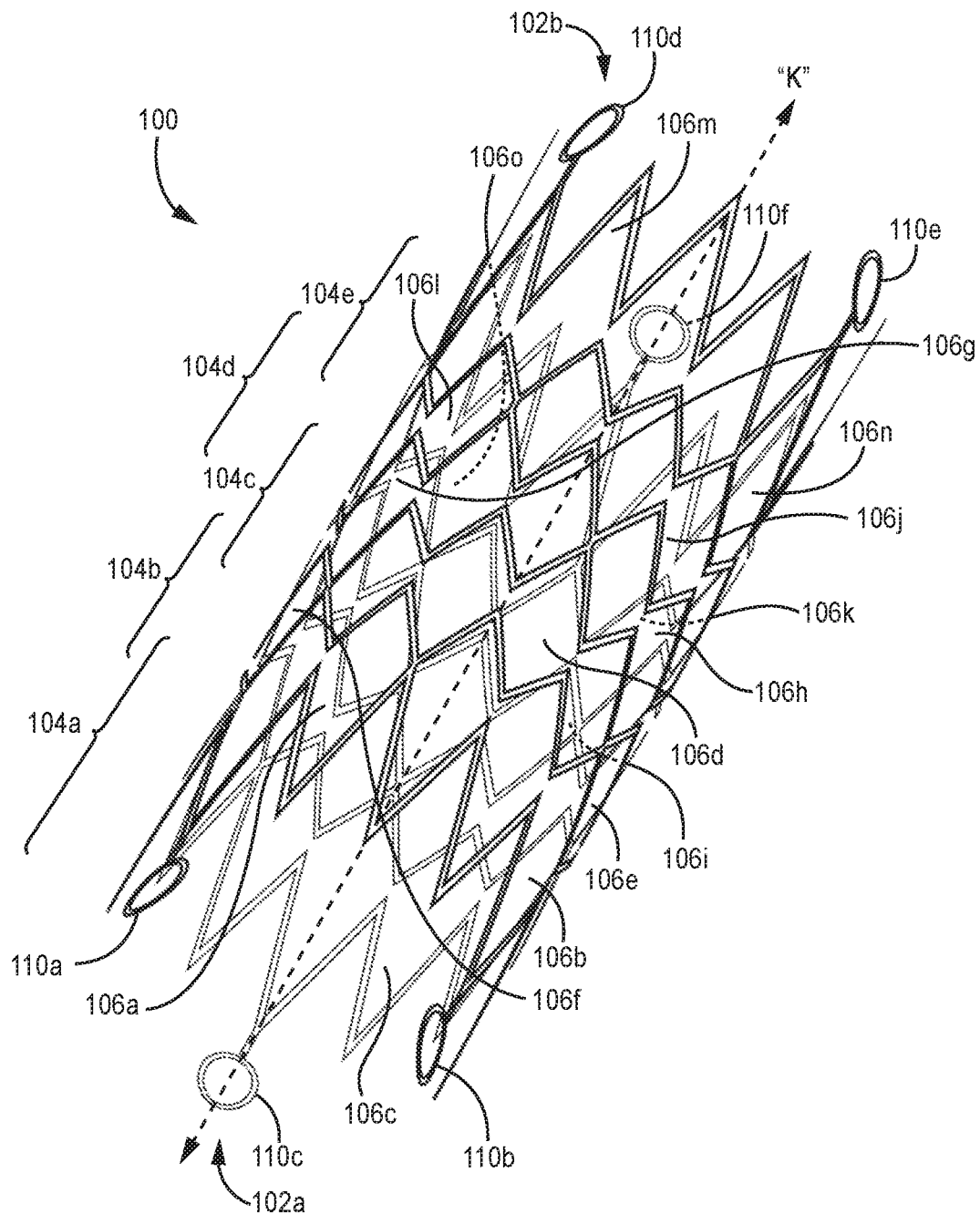
FIG. 1A is a perspective view of an example stent in an expanded condition.

A medical stent, e.g., a vascular stent or an arterial stent, may be configured such that certain mechanical characteristics of the stent, such as lateral and radial strength, fracture resistance, and uniform strain distribution, are balanced with stent flexibility in both the longitudinal and radial directions. A stent may be flexible in order to accommodate movement at the implantation site within a patient. For example, a stent may be positioned within a subject's vasculature at or near a subject's joint (e.g., hip, knee, elbow, etc.). In these regions, the stent may be subjected to torsion, bending and other mechanical stress. Moreover, stents for use in the venous system such as inferior vena cava (IVC), common iliac, external iliac, and common femoral veins regions require relatively high strength and maximum flexibility, e.g., compared with stents configured for use in other implant sites, such as arterial implant sites.

In some cases, an end of a stent may have different performance requirements than the middle of the stent (e.g., a distal or proximal end, or both the distal and proximal ends, which may be terminal ends of the stent). Flexibility, radial force (e.g., force in radially outward directions from a center axis of the stent), and lateral force (e.g., force in a single lateral direction), and durability requirements may each be somewhat different for the end of the stent than for the middle. In addition, the end may play a particularly important role with respect to ease of deployment of the stent in a body lumen of a patient and/or deployment accuracy.

The example stents described herein may accomplish particular technical advantages. For example, the modification of at least one end segment of the stent, such that it has a different configuration than the intermediate segments of the stent (located between the end segments), including longer struts (the length being measured along a longitudinal axis of the respective strut) than the intermediate segments, may improve ease of deployment and/or deployment accuracy of the stent when compared to stents without modification to any of the end segments (with the same length struts in the intermediate segments and the end segments). The configuration of the end segments of the stent may allow the stent to be deployed more smoothly (e.g., may experience less "jump") from a delivery device (e.g., a delivery catheter), such that the stent may be more easily, predictably, and accurately deployed in at an intended site within a body lumen of a patient without the stent jumping out of the delivery device (e.g., as an outer sheath is retracted) and away from the intended target site. Because at least the end segment of the stent being deployed from a delivery device first (e.g., a distal end of the stent) includes longer struts, for a given delivery speed, the stent may be deployed from the delivery device at a slower rate compared to an end segment having shorter struts, which may allow the stent to be deployed from the delivery device relatively smoothly.

Additionally, the end segments of the stents described herein may have reduced radial and lateral forces when compared to stents without modification to any of the end segments, due at least in part to the longer struts in the end segments, such that the diameter transition will be less abrupt when the end of the stent is deployed oversized in a relatively healthy portion of a vein or other body lumen.

In some examples, the length of some or all of the struts of the circumferential row of struts of the end segment closest to the end of the stent may be longer than the struts of the adjacent circumferential row of struts and/or longer than the struts of the intermediate segments. For example, the length of the struts of the circumferential row of struts closest to the end of the stent may be about one-and-a-half (1.5) times to approximately three (3) times (i.e., approximately 1.5-3 times) longer than at least one of the struts (or all of the struts) of an intermediate segment of the stent, such as approximately 1.5-2.5 times longer than the at least one of the struts (or all of the struts) of the intermediate segment of the stent, or approximately 2 times the length of the at least one of the struts (or all of the struts) of the intermediate segment of the stent. The length of the struts of the end segment may affect the radial and lateral force exhibited by the end segment. For example, the longer the strut, the less radial and lateral force the end segment may exhibit.

In some examples, a stent includes a stent body defining a longitudinal axis and proximal and distal ends. The stent body may be expandable from a compressed configuration to an expanded configuration. The stent body may include a plurality of stent segments, including a first end segment and a second end segment on opposite ends of the stent body and at least one intermediate segment disposed between the first end segment and the second end segment. Each stent segment may define a plurality of cells and a plurality of peaks and valleys. The distance between at least one pair of an adjacent peak and valley of the first end segment may be substantially equal to a first length. The distance between at least one pair of an adjacent peak and valley of the at least one intermediate segment may be substantially equal to a second length. The first length may be longer than the second length.

In some examples, the example stents may be formed by a method including selecting an appropriate diameter tubular member, forming the stent pattern described above in a tubular member to form the stent body, incrementally expanding and heat setting the tubular member, and heat setting the tube at its final diameter.

Although the figures below illustrate stents with a particular number of segments, the number of segments may vary depending on the type of interventional procedure and the desired length of the stent.

The stents of the present disclosure may have particular application in an iliofemoral vein of a patient. However, the stents may be used in any suitable location of the vasculature or other body lumen.

Figure 1B:
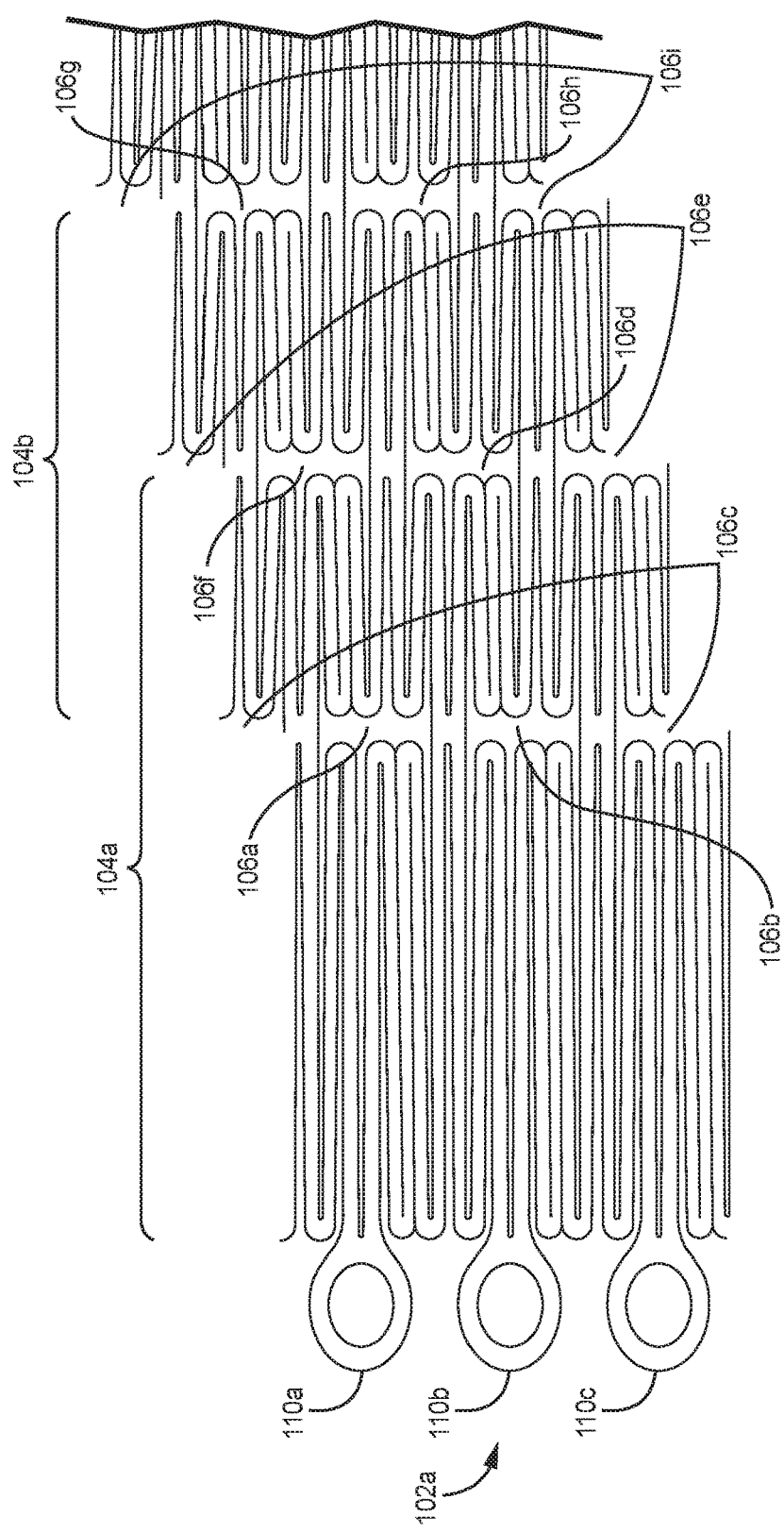
FIG. 1B is a plan view of a portion of the stent of FIG. 1A unrolled, laid flat, and in an unexpanded condition.
Figure 1C:
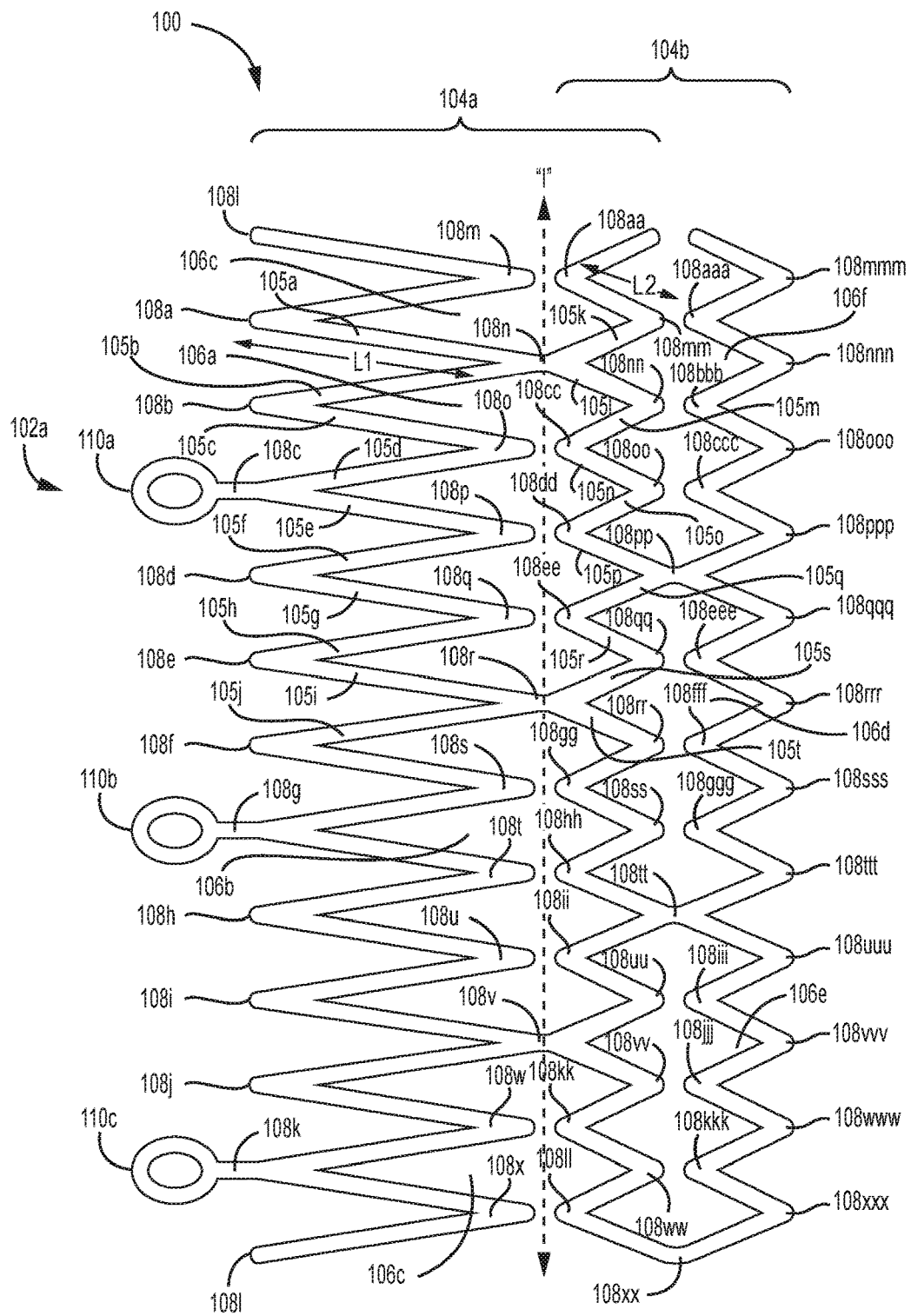
FIG. 1C is a plan view of a portion of the stent of FIG. 1A unrolled, laid flat, and in an expanded condition.

FIG. 1A is a perspective view of an example stent in an expanded condition. FIG. 1B is a plan view of a portion of the stent of FIG. 1A unrolled, laid flat, and in an unexpanded condition. FIG. 1C is a plan view of a portion of the stent of FIG. 1A unrolled, laid flat, and in an expanded condition. In the example shown in FIGS. 1A-1C, the stent comprises a stent body 100 defining a longitudinal axis "k," a proximal end 102a and a distal end 102b. The stent body 100 may be expandable from a compressed configuration, as shown in FIG. 1B, to an expanded configuration, as shown in FIGS. 1A and 1C.

In a compressed configuration, the stent body 100 may define a smaller profile (e.g., a smaller outer perimeter in a cross-section taken perpendicular to longitudinal axis "k", which may be an outer diameter in examples in which the stent body 100 is round in cross-section). The stent body 100 may be compressed for, example, before deployment at a treatment site, including when the stent body 100 is being delivered to the treatment site. The compressed configuration of the stent body 100 may allow for a lower profile delivery system, due at least in part to the smaller profile stent body 100, which may increase the ease with which the stent body 100 may be delivered to a treatment site within a body lumen.

In some examples, the stent body 100 may be biased to an expanded configuration but may be compressed and constrained, for example, by a sheath of a delivery catheter until deployment of the stent body 100 from the delivery catheter. For example, the stent body 100 may formed from a shape memory material, such as, but not limited to, a nickel titanium alloy. The stent body 100 may be deployed at a treatment site by, for example, retraction of the sheath of the delivery catheter which may allow for the stent body 100 to expand into the body lumen.

In some examples, the stent body 100 may not be biased to an expanded configuration and may be expanded at the delivery site by, for example, a balloon catheter or another mechanism suitable for expanding the stent body 100 from the compressed configuration to the expanded configuration. For example, the stent body 100 may be formed from stainless steel or another suitable non-self-expanding material.

The stent body 100 may include a plurality of stent segments 104a-104e (collectively referred to herein as "stent segments 104). Each of the stent segments may define a circumferential row of cells. Each of the stent segments 104 may be defined by a pair of adjacent circumferential rows of struts where each row of struts extends in a circumferential direction. Adjacent stent segments, such as stent segments 104a and 104b, may share a common row of struts. Example struts are shown as struts 105a-105t in FIG. 1C, and the struts of the stent body 100 may be collectively referred to as struts 105. Each of the struts 105 may be a substantially straight portion (e.g., a straight or nearly straight member) of the stent body 100 that may join with one or more other struts 105 at a vertex. For example, the strut 105b is a substantially straight portion of the stent body 100 that joins with the struts 105a, 105k, and 105l at the vertex 108n and joins with the strut 105c at the vertex 108o. As another example, the strut 105c is a straight portion of the stent body 100 that joins with the strut 105b at the vertex 108o and joins with the strut 105d at the vertex 108c. In some examples, the struts 105 may each remain substantially straight before and after expansion of the stent body 100. However, the struts 105 may move relative to each other, e.g., pivoting at the vertices relative to adjacent struts, when the stent body 100 expands from the compressed configuration to the expanded configuration.

Although the stent body 100 is illustrated in FIG. 1A as including the five overlapping stent segments 104a-104e (and three independent, non-overlapping stent segments 104a, 104c, 104e), in other examples, the stent body 100 may include any suitable number of stent segments 104 according to particular needs. For example, in applications requiring a shorter stent, the stent body 100 may include a smaller number of stent segments 104 such as three or four stent segments. As another example, in applications requiring a longer stent, the stent body 100 may include a larger number of stent segments 104. In some examples, each of the stent segments 104 may be shorter and/or longer such that a greater or fewer number of total stent segments 104 may result in a stent body 100 with the same length.

The stent segments 104 of the stent body 100 include an end segment 104a located at the proximal end 102a of the stent body 100 and an end segment 104e at the distal end 102b of the stent body 100. Each of the end segments 104a and 104e may be located at an end of the stent body 100 so that it is only adjacent one other stent segment. The stent segments 104 further include at least one intermediate segment 104b-104d disposed between the end segment 104a and the end segment 104e.

The struts of each of the stent segments 104 may define a plurality of cells 106, which may each be a closed cell defined by surrounding struts and each defining a single opening. For example, the end segment 104a may define the cells 106a-106c, the intermediate segment 104b may define the cells 106d-106f, and the end segment 104e may define cells 106m-106o.

In some examples, the terminal ends 110a-110f are configured to help retain the stent body 100 on a delivery device (e.g., configured to mate with structures on a delivery device). In addition, in some example, one or more terminal ends 110a-110f may be radiopaque or may include radiopaque elements, which may be configured to aid a clinician in visualizing the position of the stent body 100 within a body lumen.

In some examples, the struts of end segment 104a are configured to define a plurality of peaks and valleys. A peak may be a vertex 108 that, together with the adjacent struts 105 forming the vertex, points in a distal or proximal direction away from a longitudinal center of the stent segment comprising the cell. For example, the struts 105b and 105c join at the vertex 108b to form a peak pointing in a proximal direction away from a longitudinal center of the stent segment 104a. The longitudinal center of the stent segment 104a is shown by the line labeled "l" in FIG. 1C. As another example, the struts 105l and 105m join at the vertex 108nn to form a peak pointing in a distal direction away from the longitudinal center of the stent segment 104a. A valley may be a vertex that, together with the adjacent struts forming the vertex, points in a distal or proximal direction toward the longitudinal center of the stent segment comprising the cell. For example, the struts 105c and 105d join at the vertex 108o to form a valley pointing in a distal direction toward the longitudinal center of the stent segment 104a. As another example, the struts 105m and 105n join at the vertex 108cc to form a valley pointing in a proximal direction toward the longitudinal center of the stent segment 104a. In some cases, the vertex of a valley may be located at the longitudinal center of the stent segment comprising the cell. For example, the struts 105a, 105b, 105k, and 105l join at the vertex 108n at the longitudinal center of the stent segment 104a, the struts 105a and 105b form at valley pointing in a distal direction, and the struts 105k and 105l form a valley pointing in a proximal direction.

The vertices 108a-108l and 108mm-108xx may correspond to a plurality of peaks defined by the end segment 104a and the vertices 108m-108x, 108aa, 108n, 108cc-108ee, 108r, 108gg-108ii, 108v, 108kk, and 108ll may correspond to a plurality of valleys defined by the end segment 104a. In some examples, the intermediate segment 104b may define a plurality of peaks and valleys. For example, the vertices 108aa, 108n, 108cc-108ee, 108r, 108gg-108ii, 108v, 108kk, and 108ll and 108mmm-108xxx, may correspond to a plurality of peaks defined by the intermediate segment 104b and the vertices 108mm-108xx, 108aaa-198ccc, 108pp, 108eee-108ggg, 108tt, 108iii-108kkk, and 108xx may correspond to a plurality of valleys defined by the intermediate segment 104b.

In some examples, a distance between at least one pair of an adjacent peak and valley of the end segment 104a (i.e., between a peak and adjacent valley) may be substantially equal to a first length. As an example, the distance between the vertex 108a and vertex 108n, which correspond to a pair of a peak and an adjacent valley, respectively, defined by the end segment 104a, may be equal to a length "L1".

The two rows of struts forming the end segment 104a may have struts of different sizes such that the cells of the end segments 104 and/or 104e are asymmetrical about the circumferential axis "l." For example, strut 105a, as well as other struts in the row of struts including strut 105a (struts 105b, 105c, 105d, 105e, 105f, 105g, 105h, 105i, 105j, etc.) may each have a length substantially equal to the length "L1" and strut 105k, as well as other struts in the row of struts including strut 105k (struts 105l, 105m, 105n, 105o, 105p, 105q, 105r, 105s, 105t, etc.) may have a length substantially equal to the length "L2" such that the strut 105a, and other struts in the row of struts including 105a, may each be twice the length of strut 105k, and other struts in the row of struts including 105k. In some examples, a distance between at least one pair of an adjacent peak and valley of the intermediate segment 104b (i.e., between a peak and adjacent valley) may be substantially equal to a second length. For example, the distance between the vertex 108aa and the vertex 108mm, which correspond to a peak and an adjacent valley, respectively, defined by the intermediate segment 104b, may be equal to a length "L2."

In some examples, the length "L1" may be longer than the length "L2". In some examples, the length "L1" may be approximately one and a half times (1.5) to approximately three times (i.e., approximately 1.5-3 times) the length "L2." For example, the length "L1" may be 1.5-2.5 times the length "L2." In some examples, the length "L1" may be approximately two times the length "L2" (e.g., two times or within 10% of two times the length "L2"). The difference in length between "L1" and "L2" may be large enough so that the difference results in improved ease of deployment and deployment accuracy but not so large that radial or lateral force is reduced to an unacceptable level.

In some examples, each stent segment 104a-104e may define the same number of cells 106, which may be the number of cells of the particular stent segment in a circumferential direction. For example, in the illustrated example, each of the stent segments 104a-104e may define three cells: the end segment 104a defines the cells 106a, 106b, and 106c, the intermediate segment 104b defines the cells 106d, 106e, and 106f, the intermediate segment 104c defines the cells 106g, 106h, and 106i, the intermediate segment 104d defines the cells 106j, 106k, and 106l, and the end segment 104e defines the cells 106m, 106n, and 106o.

In some examples, each stent segment 104a-104e may define the same number of peaks and valleys. For example, in the illustrated example, each stent segment 104a-104e defines 24 peaks and 24 valleys. For example, the end segment 104a defines 24 peaks, and defines 24 valleys; and the intermediate segment 104b defines 24 peaks, and defines 24 valleys. In some examples, a portion of the end segment 104a defining only one cell defines only four peaks, only three valleys, and only two half valleys on each of the two opposing sides (i.e., each circumferential row of struts defining either side of the respective stent segment) of the portion of the first end segment. For example, in the illustrated example, the portion of the end segment 104a defining the cell 106a defines only four peaks, each corresponding to one of the vertices 108b, 108c, 108d, and 108e, only three valleys, each corresponding to one of the vertices 108o, 108p, and 108q, and only two half valleys, each corresponding to one of the vertices 108n and 108r on one of the two opposing sides of the portion of the end segment 104a defining the cell 106a, and defines only four peaks, each corresponding to one of the vertices 108nn, 108o, 108pp, and 108qq, only three valleys, each corresponding to one of the vertices 108cc, 108dd, and 108ee, and only two half valleys, each corresponding to one of the vertices 108n and 108r on the other of the two opposing sides of the portion of end segment 104a defining cell 106a. A half-valley may be one half of a valley, as defined by one strut defining the cell, and may combine with another half-valley, as defined by an adjacent strut defining an adjacent cell, to form the valley.

For example, the strut 105b may define one half of a valley and the strut 105a may define one half valley, such that the two half-valleys may join at the vertex 108n to form a whole valley.

In some examples, a portion of the intermediate segment 104b defining only one cell defines only four peaks, only three valleys, and only two half valleys on each of the two opposing sides of the portion of the intermediate segment. For example, in the illustrated example, the portion of the intermediate segment 104b defining the cell 106d defines only four peaks, each corresponding to one of the vertices 108ee, 108r, 108gg, and 108hh, only three valleys, each corresponding to one of the vertices 108qq, 108rr, and 108ss, and only two half valleys, each corresponding to one of the vertices 108pp and 108tt on one of the two opposing sides of the portion of the intermediate segment 104b defining the cell 106d, and defines only four peaks, each corresponding to one of the vertices 108qqq, 108rrr, 108sss, and 108ttt, only three valleys, each corresponding to one of the vertices 108eee, 108fff, and 108ggg, and only two half valleys, each corresponding to one of the vertices 108pp and 108tt on the other of the two opposing sides of the portion of the intermediate segment 104b defining the cell 106d.

The end segments of stent bodies described herein, including stent body 100 shown in FIGS. 1A-1C, may have different performance requirements than the middle of the stent body 100. For example, it may be desirable to have different radial force and lateral force (when in the expanded state) at the end segments 104a and 104e relative to the intermediate segments. For example, a lower radial and lateral force at the end segments 104a and 104e may result in a less abrupt diameter transition when the end of the stent is deployed oversized in a relatively healthy portion of a vein or other body lumen. Additionally, longer struts at the end segments 104a and 104e may improve the ease of deployment and deployment accuracy of the stent body 100 in a body lumen of a patient.

The pattern of the cells 106 of the end segments 104a and 104e of the stent body 100 as described herein, which have a different configuration than the intermediate segments of the stent body 100, which are wider, in a longitudinal direction, than the intermediate segments, may reduce radial and lateral force in the end segments 104a and 104e compared to stents with the same configuration in the end and intermediate segments, such that the diameter transition will be less abrupt when the distal end 102b of the stent body 100 is deployed oversized in a relatively healthy portion of a vein or other body lumen of a patient.

In addition, the pattern of the cells 106 of the end segments 104a and 104e of the stent body 100 as described herein, the cells 106 having a different configuration than the cells of the intermediate segments of the stent body 100, which are wider, in a longitudinal direction, than the intermediate segments, may also improve ease of deployment and deployment accuracy compared to stents with the same configuration in the end and intermediate segments. For example, the stent may be deployed more smoothly (e.g., may experience less "jump") from a delivery device, such that the stent may be more easily, predictably, and accurately deployed in an intended site within a body lumen of a patient without the stent jumping out of the delivery device and away from the intended target site.

Figure 2:
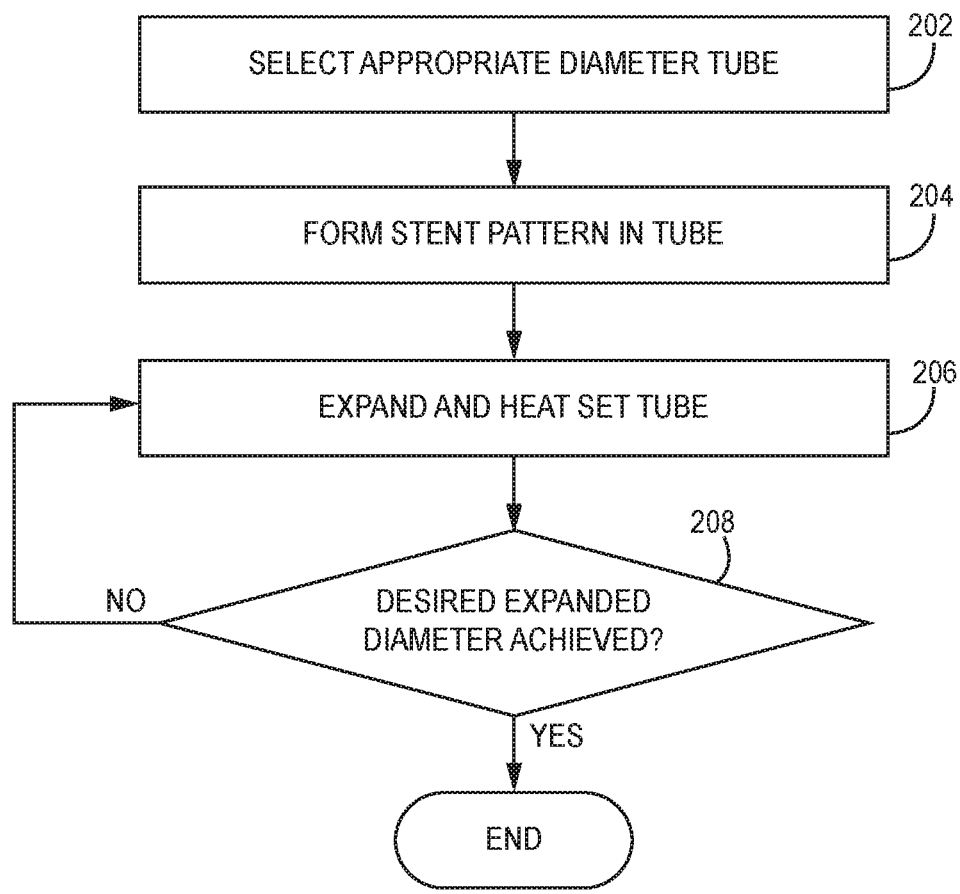
FIG. 2 is a flow diagram illustrating an example method of manufacture of the stent shown in FIGS. 1A-1C.

FIG. 2 is a flow chart illustrating an example method of manufacture of the stents shown in FIGS. 1A-1C. In accordance this process of manufacture, a tube, such as a nitinol tube having an appropriate defined diameter is selected (202). For a venous application, the stent may require a greater wall thickness relative to arterial stents, e.g., approximately 4.5 mm for the 10, 12 and 14 mm stents and approximately 7 mm for the 16, 18 and 20 mm stents. The tube is then positioned with respect to a laser. The laser, which is programmed to provide the stent segment pattern of the stent body 100 described hereinabove, is activated to form the stent segment pattern (204).

In examples in which the stent is self-expandable and, therefore, formed from a self-expanding material, the cut tube is then subjected to a shape-setting process in which the cut tube is expanded on a mandrel and then heated (206). Multiple incremental expansions and heating cycles may be used to shape-set the stent body 100 to a desired expanded diameter (208). In some examples, the final expanded diameter may be equal to the desired deployed diameter of the stent body 100. The stent body 100 may be axially restrained such that the length of stent does not change during expansion.

Figure 3:
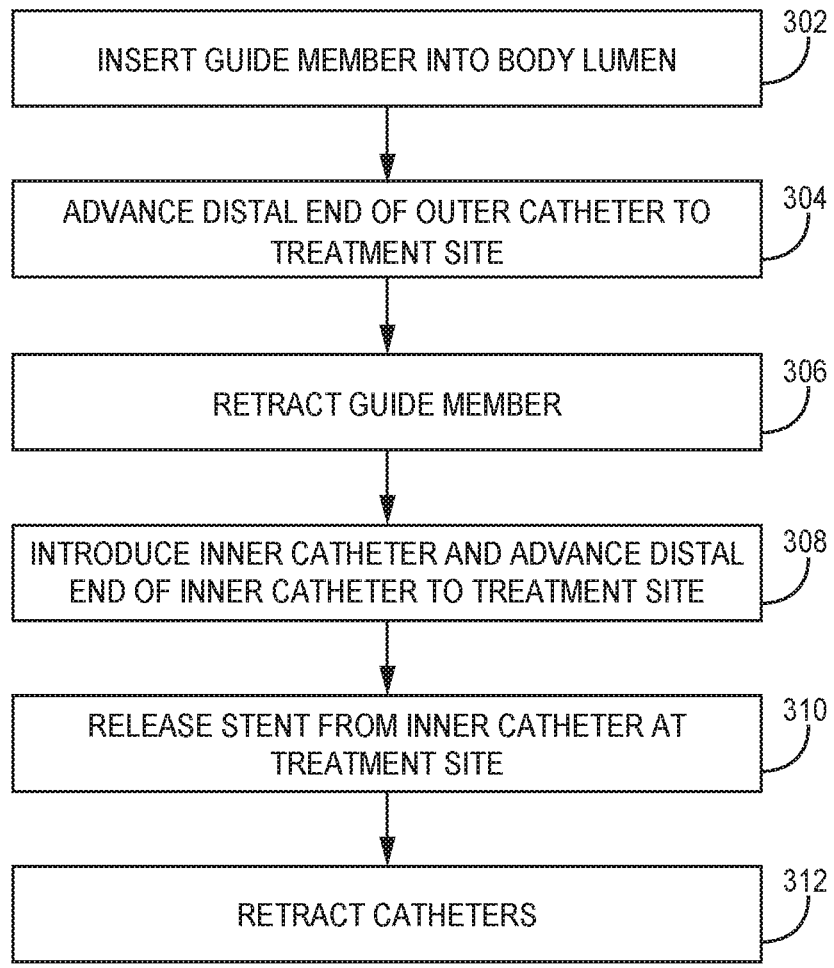
FIG. 3 is a flow diagram illustrating an example method of implanting stent shown in FIGS. 1A-1C.

FIG. 3 is a flow diagram illustrating an example method of implanting any one or more of the stents shown in FIGS. 1A-1C. A guide member may be introduced into a body lumen of a patient (302). The guide member may be advanced though the body lumen to position a leading end (distal end) of the guide member at a target location as determined by a clinician. In some examples, the guide member may include a guidewire, a guide catheter, or both a guidewire and a guide catheter.

An outer catheter may be introduced over the guide member, or, in some examples, within the guide member, and a distal portion of the outer catheter may be advanced substantially adjacent to the treatment site as determined by the clinician (304). The outer catheter may define an outer catheter lumen.

The guide member may be retracted to remove the guide member from the outer catheter lumen (306), while leaving the outer catheter in place.

In some examples, an inner catheter may be introduced within the outer catheter and a distal portion of the inner catheter may be advanced proximate to the treatment site (308). In some examples, the distal portion of an inner catheter may be advanced to be substantially aligned with the distal portion of the outer catheter. In such examples, a distal portion of the inner catheter may be secured to a stent, including the stent body 100 of FIGS. 1A-1C.

In some examples, both the outer catheter and inner catheter may be advanced to the target location simultaneously, with the inner catheter being inside the outer catheter and the stent being positioned between the inner catheter and the outer catheter. For example, the delivery device described in U.S. patent application Ser. No. 14/256,136 naming inventors Senness et al., which is entitled, "STENT DELIVERY SYSTEM" and is incorporated herein by reference in its entirety, may be used to deliver any of the stents described herein. In such examples, the outer catheter may help retain the stent relative to the inner catheter.

The stent may be released from the inner catheter lumen and to the treatment site (310). For example, in some examples, a plunger may be advanced within the inner catheter lumen to push the stent from a distal portion of the inner catheter lumen. A clinician may control the plunger to advance the plunger such that the stent is advanced from the inner catheter.

In other examples, the stent may be positioned between the inner and outer catheters, and the outer catheter may be retracted with respect to the inner catheter and stent to allow for release of the stent from the inner catheter.

As the stent is released from a distal end of the inner catheter lumen or from around an outer surface of the inner catheter, the stent may expand such that it is secured against the wall of the body lumen and anchors the stent within the body lumen. In other examples, the stent may be expanded via a balloon or other mechanism.

After satisfactory delivery of the stent, other elements, including, for example, the outer catheter, an inner catheter, and/or a plunger may be removed from the body lumen (312).

Various examples have been described. These and other examples are within the scope of the following claims.

What is claimed is:

1. A stent comprising:
a stent body defining a proximal end, a distal end, and a longitudinal axis extending from the distal end to the proximal end, the stent body being expandable from a compressed configuration to an expanded configuration, the stent body including a plurality of stent segments,
wherein the stent segments include a first end segment and a second end segment on opposite ends of the stent body and at least one intermediate segment disposed between the first end segment and the second end segment,
wherein each stent segment defines a plurality of cells,
wherein the first end segment defines a plurality of peaks and valleys, the distance between a peak and an adjacent valley of the first end segment being equal to a first length,
wherein the at least one intermediate segment defines a plurality of peaks and valleys, the distance between a peak and an adjacent valley of the at least one intermediate segment being equal to a second length,
wherein the first length is longer than the second length,
wherein, for each of the plurality of the peaks and the valleys of the first end segment, a distance between the peak and the adjacent valley is longer than the second length,
wherein the first end segment includes a first circumferential row of struts and a second circumferential row of struts defining cells of the first end segment, the second circumferential row of struts being directly adjacent to the first circumferential row of struts,
wherein the first circumferential row of struts defines a first peak and a first valley, wherein the second circumferential row of struts defines a second peak and a second valley, wherein the first peak points away from a longitudinal center of the first end segment and the first valley points towards the longitudinal center of the first end segment, wherein the second peak points towards the longitudinal center of the first end segment and the second valley points away from the longitudinal center of the first end segment, and
wherein the first circumferential row of struts and the second circumferential row of struts are connected to each other between the first valley and the second peak, the connection between the first valley and the second peak being substantially parallel to the longitudinal axis of the stent body.

2. The stent of claim 1, wherein the first length is approximately two times the second length.

3. The stent of claim 1, wherein the first length is 1.5-3 times the second length.

4. The stent of claim 1, wherein each stent segment defines the same number of cells.

5. The stent of claim 1, wherein each stent segment defines the same number of peaks and valleys.

6. The stent of claim 1, wherein a portion of the first end segment defining only one cell defines only four peaks, only three valleys, and only two half valleys on each of two opposing sides of the portion of the first end segment.

7. The stent of claim 1, wherein a portion of the at least one intermediate segment defining only one cell defines only four peaks, only three valleys, and only two half valleys on each of two opposing sides of the portion of the intermediate segment.

8. A method comprising:
forming a stent pattern in a tubular member to form a stent body defining a proximal end, a distal end, and a longitudinal axis extending from the distal end to the proximal end, the stent body being expandable from a compressed configuration to an expanded configuration, the stent body including a plurality of stent segments,
wherein the stent segments include a first end segment and a second send segment on opposite ends of the stent body and at least one intermediate segment disposed between the first end segment and the second end segment,
wherein each stent segment defines a plurality of cells,
wherein the first end segment defines a plurality of peaks and valleys, the distance between a peak and an adjacent valley of the first end segment being equal to a first length,
wherein the at least one intermediate segment defines a plurality of peaks and valleys, the distance between a peak and an adjacent valley of the at least one intermediate segment being equal to a second length,
wherein the first length is longer than the second length,
wherein, for each of the plurality of the peaks and the valleys of the first end segment, a distance between the peak and the adjacent valley is longer than the second length,
wherein the first end segment includes a first circumferential row of struts and a second circumferential row of struts defining cells of the first end segment, the second circumferential row of struts being directly adjacent to the first circumferential row of struts,
wherein the first circumferential row of struts defines a first peak and a first valley, wherein the second circumferential row of struts defines a second peak and a second valley, wherein the first peak points away from a longitudinal center of the first end segment and the first valley points towards the longitudinal center of the first end segment, wherein the second peak points towards the longitudinal center of the first end segment and the second valley points away from the longitudinal center of the first end segment, and
wherein the first circumferential row of struts and the second circumferential row of struts are connected to each other between the first valley and the second peak, the connection between the first valley and the second peak being substantially parallel to the longitudinal axis of the stent body.

9. The method of claim 8, wherein the tubular member comprises shape-memory material.

10. The method of claim 8, further comprising incrementally expanding and heat setting the tubular member.

11. The method of claim 8, wherein the first length is approximately two times the second length.

12. The method of claim 8, wherein the first length is 1.5-3 times the second length.

13. The method of claim 8, wherein each stent segment defines the same number of cells.

14. The method of claim 8, wherein each stent segment defines the same number of peaks and valleys.

15. The method of claim 8, wherein a portion of the first end segment defining only one cell defines only four peaks, only three valleys, and only two half valleys on each of two opposing sides of the portion of the first end segment.

16. The method of claim 8, wherein a portion of the at least one intermediate segment defining only one cell defines only four peaks, only three valleys, and only two half valleys on each of two opposing sides of the portion of the intermediate segment.

17. A method comprising:
   advancing a distal end of a catheter to a treatment site within a patient, wherein a stent is disposed within the catheter; and
   releasing the stent from the catheter at the treatment site, the stent comprising:
      a stent body defining a proximal end, a distal end, and a longitudinal axis extending from the distal end to the proximal end, the stent body being expandable from a compressed configuration to an expanded configuration, the stent body including a plurality of stent segments,
      wherein the stent segments include a first end segment and a second end segment on opposite ends of the stent body and at least one intermediate segment disposed between the first end segment and the second end segment,
      wherein each stent segment defines a plurality of cells,
      wherein the first end segment defines a plurality of peaks and valleys, the distance between a peak and an adjacent valley of the first end segment being equal to a first length,
      wherein the at least one intermediate segment defines a plurality of peaks and valleys, the distance between the peak and an adjacent valley of the at least one intermediate segment being equal to a second length,
      wherein the first length is longer than the second length,
      wherein, for each of the plurality of the peaks and the valleys of the first end segment, a distance between the peak and the adjacent valley is longer than the second length,
      wherein the first end segment includes a first circumferential row of struts and a second circumferential row of struts defining cells of the first end segment, the second circumferential row of struts being directly adjacent to the first circumferential row of struts,
      wherein the first circumferential row of struts defines a first peak and a first valley, wherein the second circumferential row of struts defines a second peak and a second valley, wherein the first peak points away from a longitudinal center of the first end segment and the first valley points towards the longitudinal center of the first end segment, wherein the second peak points towards the longitudinal center of the first end segment and the second valley points away from the longitudinal center of the first end segment, and
      wherein the first circumferential row of struts and the second circumferential row of struts are connected to each other between the first valley and the second peak, the connection between the first valley and the second peak being substantially parallel to the longitudinal axis of the stent body.

18. The method of claim 17, further comprising:
   inserting a guide member into a body lumen of the patient; and
   advancing the distal end of the catheter to the treatment site over the guide member.

19. The method of claim 17, wherein the first length is approximately two times the second length.

20. The method of claim 17, wherein the first length is 1.5-3 times the second length.

21. The method of claim 17, wherein each stent segment defines the same number of cells.

22. The stent of claim 1, wherein the connection between the first valley and the second peak is at a common vertex of the first valley and the second peak.

23. The stent of claim 1, wherein the at least one intermediate segment includes the second circumferential row of struts and a third circumferential row of struts defining cells of the at least one intermediate segment, the second circumferential row of struts being directly adjacent to the third circumferential row of struts, wherein the third circumferential row of struts includes a third peak and a third valley, the third peak pointing towards the longitudinal center of the intermediate segment and the third valley pointing away from the longitudinal center of the intermediate segment, and wherein the second circumferential row of struts and the third circumferential row of struts are connected to each other between the second valley and the third peak, the connection between the second valley and the third peak being substantially parallel to the longitudinal axis of the stent body.

24. The stent of claim 23, wherein the connection between the second valley and the third peak is at a common vertex of the second valley and the third peak.

* * * * *